United States Patent [19]

Klein et al.

[11] 4,412,027
[45] Oct. 25, 1983

[54] THICKENED KETONE COMPOSITIONS

[75] Inventors: Kenneth Klein, Old Bridge; Patricia E. Bator, Secaucus, both of N.J.; Harry H. Pact, Norwalk, Conn.

[73] Assignee: Henkel Corporation, Minneapolis, Minn.

[21] Appl. No.: 284,145

[22] Filed: Jul. 16, 1981

[51] Int. Cl.$^3$ ............................................. C08K 5/07
[52] U.S. Cl. .................................................... 524/364
[58] Field of Search ................... 260/29.6 SQ, 32.8 R; 524/361, 364

[56] References Cited

U.S. PATENT DOCUMENTS 3,931,089 1/1976 Karl ............................ 260/29.6 HN
4,065,422 12/1977 Lundmark et al. ..................... 525/1

Primary Examiner—Joseph L. Schofer
Assistant Examiner—N. Sarofim
Attorney, Agent, or Firm—Forrest L. Collins

[57] ABSTRACT

This invention describes compositions in which normally fluid ketones are rendered viscous by a polymer.

10 Claims, No Drawings

THICKENED KETONE COMPOSITIONS

BACKGROUND OF THE INVENTION

1. Field of the Invention

The present invention describes methods for increasing the viscosity of a ketone containing composition.

2. Description of the Art Practices

It is known from U.S. Pat. No. 3,931,089 issued Jan. 6, 1976 to Karl et al that acid solutions containing homopolymers of 2-acrylamido-2-methylpropanesulfonic acid and its salts may be used to thicken aqueous solutions. Such compositions were described as being useful in the controlled release of viscous acidic liquids, such as retarding the action of acids on limestone during acidizing of oil wells.

It was later discovered by Lundmark et al in U.S. Pat. No. 4,065,422 issued Dec. 27, 1977 that homopolymers of 2-acrylamido-2-methylpropanesulfonic acid salts could be used to impart lubricity to kerationous substrates such as skin or hair or upon mucous membranes to impart a lubricated feel. Such compositions were stated to have utility in diverse personal care products such as hand and body creams, soap bars, suntan lotion, preelectric shave skin conditioners aftershave lotions, lip balms, cold creams, bubble baths, cleansing and lotion pads, douches and vaginal lubricants. Similar products are described in U.S. Pat. No. 4,065,422 issued Dec. 27, 1977 to Lundmark et al comprising as an additional ingredient a monohydric alcohol. Such compositions were desirable where it was necessary to thicken an alcohol containing product to obtain the proper viscosity for the desired use.

It is now been found that if a ketone is desolved in a miscible solvent which is compatible with a homopolymer of a salt of 2-acrylamido-2-methylpropanesulfonic acid that the ketone will be retained in the solution and will have its viscosity raised substantially. This is particularly important in that for certain applications, particularly in nail polish removers, the ketones tend to be of very low viscosity and volatility and are therefore of limited utility.

It will be observed when working with ordinary nail polish removers that the runny product first has a potential to spill upon clothing or furniture thus damaging the finish of both. Also, the solvating effect of the ketone when removing nail polish allows any completely uncured lacquer in the nail polish to become solubilized. Hence, unless the lacquer is effectively and cleanly removed, it may also drip onto carpeting and the like causing permanent stains.

Therefore, there exists a need to prepare a thickened ketone containing composition. During the course of making the present invention, the author has discovered that additional ketones other than the most likely solvents for nail polish remover compositions have their viscosity raised substantially when included in a solution in which the ketone is miscible with the polymer of the present invention.

Throughout the specification and claims, percentages and ratios are by weight and temperatures are given in degrees Celsius unless otherwise indicated. While not being limiting, the term low viscosity ketone refers to any ketone which is liquid at room temperature, is treated by solvent or other action to become liquid at room temperature. Other action may include heating.

SUMMARY OF THE INVENTION

A composition having a ketone in a thickened state comprising:
(a) a low viscosity ketone;
(b) a solvent in which the ketone is miscible selected from the group consisting of water and alcohols and mixtures thereof; and
(c) a homopolymeric salt of 2-acrylamido-2-methylpropanesulfonic acid in an amount sufficient to thicken the composition.

DETAILED DESCRIPTION OF THE INVENTION

The present invention first requires a salt of 2-acrylamido-2-metylpropanesulfonic acid. Such polymers are adequately described in U.S. Pat. No. 4,065,422 which is herein incorporated by reference together with the previously cited art.

In particular, the polymer is prepared by obtaining a monomer having the formula

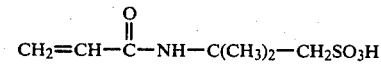

The polymerization reaction may be accomplished by solution, emulsion or suspension polymerization processes. The medium for the polymerization is conveniently water, a monohydric alcohol, or a mixture thereof. The choice of the medium is best dictated by the requirements of the final end product to be formulated.

The polymerization reaction is described as temperature, pH, and catalyst sensitive. In addition it is desirable to exclude oxygen from the reaction vessel used to form the polymer as that material inhibits the polymerization process. The catalysts which are included to enhance the rate of polymerization are materials such as ammonium bisulfite, ferrous sulfate, hydrogen peroxide, sodium metabisulfite, or other redox catalysts.

The polymer may be varied in molecular weight by controlling the amount of the catalyst, the pH, or the rate of addition of the monomer to the reaction vessel. The polymerization may be facilitated by converting the monomer from its acid form to a salt which is water-soluble. This step is quite desirable where the end use of the polymer is in a personal care product. That is, the in use pH of the personal care product should be from about 3 to about 10, preferably about 4.5 to about 9.0 and most preferably from about 5 to about 8. Thus within the foregoing ranges some of the polymer may be in the acid form. The salts of the polymer preferably contain as cations, sodium, potassium, ammonium, monoethanolamine, diethanolamine, triethanolamine and 2-amino-2-methyl-1-propanol as well as mixtures thereof. The foregoing list is merely exemplary of salts which may be used. Also within the scope of the present invention are water-insoluble salts where the product is not adversely affected by precipitation of the polymer. Examples of suitable water-insoluble salts are calcium and magnesium.

As was previously mentioned, the molecular weight of the polymer may be controlled by the pH, the rate of addition of the monomer or the judicious use of the catalyst. It has been found desirable to utilize the aforedescribed polymers having a molecular weight of from about 1,000,000 to about 5,000,000; more preferably from about 2,500,000 to about 4,500,000 to increase the asthetics of the composition. That is, it has been found that extremely high molecular weight polymers of the type described may result in a pituitive or stringly consistency of the end product. It has therefore been found desirable to limit the pituitiveness by selecting the preferred molecular weight range. To this end any common chain transfer agent such as mercaptosuccinic acid may be used to limit the molecular weight of the polymer. A suitable polymer for use in the present invention falling within the above parameters is HSP 1180 available from the Henkel Corporation.

It is noted that the terminal groups on the polymer have little bearing on the desired properties of the products and are thus not specified. In the interest of complete disclosure it is noted that the terminal groups are most often hydrogen, but may also be hydroxyl, sulfate, sulfonate or

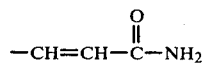

$$-CH=CH-\overset{O}{\underset{\|}{C}}-NH_2$$

The next element of the prsent invention is the ketone which is to be thickened. It is first noted that it is somewhat surprising in that the ketone alone when mixed with the polymer causes the polymer to precipitate out. Thus, the effectiveness of the polymer as a thickening agent is lost. It was somewhat surprisingly found that ternary mixtures of the ketone, polymer and water and/or an alcohol as later described performed eminently well.

The ketones which are utilized in the present invention may be any ketone, preferably a mono-keto compound particularly those short chain ketones such as, dimethylketone (acetone) and methylethylketone. Of course, other higher ketones may also be used provided that they are sufficiently liquid or dispersable in the later described solvent.

The solvent utilized in the present invention is conveniently water or alcohol or mixtures thereof. The alcohols are preferably lower alcohols such as: methanol, ethanol, n-propanol, isopropanol and the like. It is of course also possible to include the higher alcohols such as lauryl, myristyl, cetyl and stearyl as well as unsaturated alcohols such as oleyl. It is also possible to vary the mixtures so that water and alcohol mixtures are used. Occasionally, additional solubilizing agents are required where the higher normally solid alcohols are employed.

The products of the present invention are formulated by simply combining the various ingredients in the amounts desired and thereafter by thoroughly mixing the components.

The preferred amounts of the components of the present invention are from about 45 percent to about 89 percent, preferably from about 57 percent to about 67 percent by weight of the ketone. The solvent is present at from about 10 percent to about 50 percent by weight, preferably from about 15 percent to about 30 percent by weight. The polymer of the 2-acrylamido-2-methylpropanesulfonic acid salt is present at from about 1 percent to about 10 percent, preferably from about 2 percent to about 7 percent by weight.

The following are examples of the present invention and are carried out by combining the ingredients and mixing.

EXAMPLE I

| | % | |
|---|---|---|
| Dimethyl Ketone | 67.0 | |
| HSP 1180* | 4.95 | |
| H₂O | 28.05 | |
| | 100.00% | viscosity cps at 25° C. 1100 cps |

*The polymer is used as an aqueous solution and measured on 100 percent solid basis.

EXAMPLE II

| | % | |
|---|---|---|
| Dimethyl Ketone | 57.00 | |
| H₂O | 28.05 | |
| HSP 1180 | 4.95 | |
| SDA 40 Alcohol | 10.0 | |
| | 100.00% | viscosity: 940 cps |

EXAMPLE III

| | % | |
|---|---|---|
| Dimethyl Ketone | 70.00 | |
| H₂O | 19.00 | |
| HSP 1180 | 1.00 | |
| SDA 40 Alcohol | 10.00 | |
| | 100.00% | viscosity: 40 cps |

EXAMPLE IV

| | % | |
|---|---|---|
| Dimethyl Ketone | 80.0 | |
| HSP 1180 | 1.0 | |
| Water | 9.0 | |
| SDA 40 Alcohol | 10.0 | |
| | 100.0 | viscosity: 40 cps |

EXAMPLE V

| | % | |
|---|---|---|
| Dimethyl Ketone | 70.0 | |
| HSP 1180 | 1.0 | |
| 3A Ethyl Alcohol | 10.0 | |
| Water | 19.0 | |
| | 100.0% | viscosity: 40 cps |

EXAMPLE VI

| | % | |
|---|---|---|
| Methyl Ethyl Ketone | 57.00 | |
| HSP 1180 | 5.00 | |
| SDA-40 Alcohol | 10.00 | |
| Water | 28.00 | |
| | 100.00% | viscosity: 80 cps |

EXAMPLE VII

| | % | |
|---|---|---|
| Methyl Ethyl Ketone | 57.0 | |
| HSP 1180 | 5.0 | |
| Water | 38.0 | |
| | 100.0% | viscosity: 80 cps |

EXAMPLE VIII

| | % |
|---|---|
| Dimethyl Ketone | 57.0 |
| HSP 1180 | 5.0 |
| Water | 28.0 |
| Isopropyl Alcohol | 10.0 |

EXAMPLE VIII-continued

| | % | |
|---|---|---|
| | 100.0% | viscosity: 850 cps |

EXAMPLE IX

| | % | |
|---|---|---|
| Methyl Ethyl Ketone | 57.0 | |
| HSP 1180 | 5.0 | |
| Isopropyl Alcohol | 10.0 | |
| Water | 28.0 | |
| | 100.0% | viscosity: 80 cps |

What is claimed is:

1. A process for removing nail polish from a nail comprising solvating the polished nail with a composition comprising:
   (a) a low viscosity ketone;
   (b) a solvent in which the ketone is miscible selected from the group consisting of water and alcohols and mixtures thereof; and
   (c) a homopolymeric salt of 2-acrylamido-2-methyl-propanesulfonic acid in an amount sufficient to thicken the composition
thereby removing the nail polish from the nail.

2. The process of claim 1 containing from about 1 percent to about 10 percent by weight of component (c).

3. The process of claim 1 wherein component (b) is a lower alcohol containing from about 1 to about 4 carbon atoms.

4. The process of claim 1 containing from about 45 percent to about 89 percent by weight of component (a).

5. The process of claim 2 containing from about 2 percent to about 7 percent by weight of component (c).

6. The process of claim 1 wherein component (b) is water.

7. The process of claim 3 wherein component (b) is ethanol.

8. The process of claim 1 wherein component (b) is present at from about 10 percent to about 50 percent by weight.

9. The process of claim 1 wherein component (c) has a molecular weight of from about 1 million to about 5 million.

10. The process of claim 1 wherein the ketone is acetone.

* * * * *